United States Patent [19]

Chignac et al.

[11] 4,127,607
[45] Nov. 28, 1978

[54] PROCESS FOR THE PREPARATION OF AN ACETAMIDE DERIVATIVE

[75] Inventors: Michel Chignac, Sisteron; Claude Grain, Volonne; Charles Pigerol, Saint-Ouen, all of France

[73] Assignee: Labaz, Paris, France

[21] Appl. No.: 800,345

[22] Filed: May 25, 1977

[30] Foreign Application Priority Data

Mar. 15, 1977 [FR] France .................. 77 07586

[51] Int. Cl.² .................. C07C 103/127
[52] U.S. Cl. .................. 260/561 R
[58] Field of Search .................. 260/561, 561 R

[56] References Cited

FOREIGN PATENT DOCUMENTS 2,442M 4/1964 France.

OTHER PUBLICATIONS

Keil, Z. Physiol Chem. 282 (1947), pp. 137–142.

Hessler et al., J. Am. Chem. Soc. 43, pp. 205–207.
Sarel et al., J. Am. Chem. Soc. 78, pp. 5416–5420.
Sperber et al., J. Am. Chem. Soc. 70, pp. 3091–3094.
Tsai et al., J. Am. Chem. Soc. 70, pp. 2530–2533.

*Primary Examiner*—Arthur P. Demers
*Attorney, Agent, or Firm*—Warren D. McPhee

[57] ABSTRACT

Process for preparing di-n-propyl acetamide of the formula:

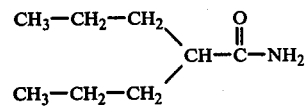

whereby di-n-propyl acetonitrile is hydrolyzed by means of 80% sulphuric acid aqueous solution in the proportion of 2 to 2.5 g of dilute acid/g of nitrile, at a temperature between 80° C and 130° C to obtain the desired amide.

2 Claims, No Drawings

PROCESS FOR THE PREPARATION OF AN ACETAMIDE DERIVATIVE

The present invention relates generally to a novel process for the preparation of an acetamide derivative, and also to the derivative obtained by this process.

The invention is more particularly concerned with a new process for the preparation of di-n-propyl acetamide of the formula:

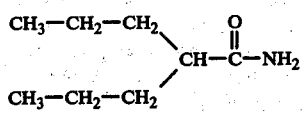

Di-n-propyl acetamide is a known product which has pharmacological properties as illustrated in B.S.M. (French Special Medicament Patent) No. 2,442 M, and in particular outstanding anti-convulsive properties.

At the present time, di-n-propyl acetamide is widely used commercially as an anti-epileptic agent. Furthermore, it has given rise to a novel class of neuropsychotropic agents, the psychorthotic agents or stabilisers of the cerebral function. In this respect, di-n-propyl acetamide is capable of stabilising the thymia without excitation or sedation and of regulating disturbed mental functions, both as regards behaviour and psyche.

One of the most conventional and the most widely used methods for the preparation of di-n-propyl acetamide consists in treating diethyl malonate under pressure and in a methanolic medium, first with sodium methylate and then with allyl chloride, these two reactions each being effected in accordance with two different methods of operation.

The diethyl diallyl malonate is then saponified with sodium hydroxide and the resulting salt is acidified to provide diallyl malonic acid, which is decarboxylated by heating to diallyl acetic acid, which is itself thereafter hydrogenated on palladised carbon to di-n-propyl acetic acid.

This latter acid is then transformed into its chloride, which is then treated with ammonia to provide finally di-n-propyl acetamide. This process is characterised by a large number of steps to be carried out, starting from the malonate, a total, in fact, of seven steps, of which the first comprises two phases. Furthermore, the operating conditions which have to be respected raise difficulties of a technical nature, such as heating under pressure during the first stage, hydrogenation on a catalyst and preparation of a generally toxic acyl chloride, which very often creates safety problems for the personnel concerned in the manufacture.

Moreover, secondary reactions may cause the formation of impurities, for example, 2-allyl valerolactone concurrently with diallyl malonic acid, and it is necessary for these impurities to be eliminated.

All these disadvantages have an unfavourable influence on the yield and the production cast of the final product.

Finding a process for the preparation of di-n-propyl acetamide which obviates all these disadvanteges is therefore of paramount importance.

Hitherto, the synthesis of acetamide substitued in the α-position by two propyl groups, starting from the corresponding nitrile has only been studied in the case where each of the two propyl groups is an isopropyl radical. Attempts to obtain diisopropyl acetamide from diisopropyl acetonitrile have been described by SAREL and collaborators in J. Am. Chem. Soc., vol. 78, pages 5416–5420 (1956) and by TSAI and collaborators in J. Am. Chem. Soc., vol. 79, pages 2530–2533 (1957).

In accordance with their method, SAREL and collaborators prepare diisopropyl acetamide by hydrolysing diisopropyl acetonitrile by means of an aqueous solution of 96% sulphuric acid (2.1 g of dilute acid/g of nitrile) for 30 minutes at the temperature of 145°–155° C.

For their part, TSAI and collaborators also prepare diisopropyl acetamide by hydrolysing diisopropyl acetonitrile for 30 minutes, but by means of 75% sulphuric acid aqueous solution (1.7 g of dilute acid/g of nitrile) and at the temperature of 140° C.

In view of the great similarity in chemical structure between diisopropyl acetamide and di-n-propyl acetamide, attempts have been made to apply to the preparation of this latter compound the processes referred to above for the preparation of the diisopropyl acetamide.

Using the exact operating conditions proposed by TSAI and collaborators, the crude di-n-propyl acetamide has been prepared with a yield of 86.1%, titrating 81.3% of pure product, which represents a final yield equal to 69.9% of pure di-n-propyl acetamide. Moreover, the crude product contains up to 18.5% of di-n-propyl acetic acid as impurity. On the other hand, following the operating conditions described by SAREL and collaborators in the aforementioned reference, an absolutely zero yield of di-n-propyl acetamide was obtained, the product of the hydrolysis reaction caramelising with a strong odour of sulphur dioxide during the synthesis.

It has now been discovered quite unexpectedly that it is possible to obtain di-n-propyl acetamide by hydrolysing di-n-propyl acetonitrile with aqueous sulphuric acid but with yields far superior to those obtained by the processes suggested by the prior art, these yields coming close to 90% of pure product and even to 96% after recycling. Thus, in accordance with the process of the invention, di-n-propyl acetamide is prepared by hydrolysing di-n-propyl acetonitrile by means of an 80% sulphuric acid aqueous solution, in the proportion of 2 to 2.5 g of dilute acid/g of nitrile, and at a temperature between 80° C. and 130° C.

For the hydrolysis reaction, the preferred temperature will be between 80° and 85° C. as this alone enables yields of 90% of di-n-propyl acetamide to be attained.

Likewise, a ratio of 2.5 g of dilute acid/g of nitrile is recommended and the reaction will be carried out for a period of 60 to 90 minutes.

The initially used di-n-propyl acetonitrile is a known product, having been cited, for example, in Z. Physiol. Chem. 282, pages 137–142 (1947).

It can be prepared, for instance, from a cyanacetic ester such as for example the methyl or ethyl ester by introducing, at a temperature between 45° and 55° C., sodium n-propylate in n-propanol medium into a reaction medium containing the cyanacetic ester in question and n-propyl bromide or iodide and keeping the temperature at reflux for about 3 hours. The di-n-propyl cyanacetic ester thus formed is then saponified with a 10 to 20% solution of sodium or potassium hydroxide at a temperature between 60° and 70° C. for 3 hours and thereafter the resulting salt is acidified with a strong acid, such as for example 36% hydrochloric acid, at a temperature a little below 40° C., so as to obtain the crude di-n-propyl cyanacetic acid, which is decarboxylated by heating to a temperature between 140° C. and 190° C.

The saponification phase may be carried out in the presence of a quaternary ammonium, such as for example trimethyl cetyl ammonium bromide.

This method of procedure enables the time for hydrolysis of the ester function to be reduced and to avoid to a maximum extent the hydolysis of the nitrile function of the di-n-propyl cyanacetic ester.

Following this process, it is possible to obtain the pure di-n-propyl acetonitrile with a yield of at least 85%, calculated on the basis of the cyanacetic ester. The process described above for the preparation of the starting di-n-propyl acetonitrile furthermore enables this product to be obtained with a minimum degree of contamination by valeronitrile and ethyl propyl acetonitrile. These impurities are, in fact, particularly troublesome and must be eliminated.

The initial cyanacetic esters are known products, having been published in J. Am. Chem. Soc. 43, 205–208 (1921).

The excellent results achieved in obtaining di-n-propyl acetamide in accordance with the process of the invention are all the more surprising, since tests carried out subsequently in which at least one of the operating conditions of the prior art was maintained, have failed to reproduce results similar to those obtained in accordance with the process of the invention.

Thus, the hydrolysis of the di-n-propyl acetonitrile with sulphuric acid was carried into effect in accordance with the reaction procedure indicated below, in which the following parameters were caused to vary:
molar ratio of sulphuric acid/nitrile
concentration of the sulphuric acid employed,
hydrolysis time,
temperature of hydrolysis of the nitrile.

Into a 500 ml spherical flash was introduced the quantity of sulphuric acid with the dilution chosen for the test. While stirring, 125.2 g of di-n-propyl acetonitrile were added in about 15 minutes and at a temperature equal to or lower than 40° C. The hydrolysis was then carried out under the conditions selected for the test:
time of the rise in temperature,
hydrolysis temperature,
time for which temperature was maintained.

The flask was cooled to room temperature and the reaction medium was poured progessively while being cooled into a 2000 ml spherical flask containing, with stirring, a sufficient quantity of iced pure water so as to obtain sulphuric acid in a concentration of approximately 16%.

During this operation, the temperature of the mixture was limited to 25° C. The mixture was cooled and the crystals were suction-filtered after being kept for one hour at a temperature of 0° to −5° C.

The crystals were rinsed on a Buchner funnel by means of two fractions, each of 125g, of iced pure water and then the mass of moist product was taken up in a 1000 ml spherical flask containing 620 g of toluene. The mixture was brought while stirring to the reflux temperature of the toluene/water azeotrope (B.P. 84° C.) until complete dissolution occurred.

The lower aqueous phase was poured off, the organic layer washed under reflux for 15 to 30 minutes while being stirred and then 6.25 g of sodium bicarbonate were decanted with 125 g of purified water, and then with as many fractions of 125 g of purified water as were necessary to remove the sulphate ions from the effluent. The toluenic solution was then treated under reflux for 30 minutes with 4.4 g of active carbon, while the water was eliminated by means of a Dean-Stark system. Filtration was carried out, followed by rinsing under heat with 62 g of toluene. The filtrate and the rinsing liquid were combined in a second 1000 ml spherical flask, crystallisation was carried out by icing and while stirring and suction-filtration was undertaken after maintaining a temperature between −5° C. and −10° C. for 2 hours. Rinsing was performed on a Buchner funnel by means of two fractions, each of 62 g of filtered and iced toluene. Suction-filtration was effected to the maximum extent, followed by drying to a constant weight in a ventilated oven at 50° C. In this way, a first fraction of di-n-propyl acetamide was obtained.

Finally, the toluenic mother liquors from the suction-filtration and rinsing operations were then brought to dryness under reduced pressure (50° C./20 mm.Hg.). In this way, a dry extract formed of di-n-propyl acetamide was obtained.

The following table shows the results obtained according to the operating conditions proposed by the prior art:

TABLE

| Sulphuric acid used: | | Conditions as regards time and temperature | | | | Yields of pure di-n-propyl acetamide |
|---|---|---|---|---|---|---|
| Concentration (weight of acid/ weight of water) | Ratio weight of dilute acid/ nitrile | Time of temperature rise | Reaction temperature | Holding time | Wt. of water to have 16 % $H_2S_4O$ | |
| 221 g  75 % | 1.76 | 30 min. | 145–150° C | 20 min. | 820 g | 112.1 g (78.6 %) |
| 265 g  96 % | 2.1 | 45 min. | 145–155° C | 30 min. | 1325 g | 0 g (0 %) |
| 312 g  80 % | 2.5 | 30 min. | 145–150° C | 20 min. | 1250 g | 104.3 g (72.8 %) |
| 265 g  96 % | 2.1 | 30 min. | 80–85° C | 90 min. | 1325 g | 111.3 g (77.7 %) |

Comparison tests carried out with the process of the invention provided the following results:

| | | | | | | |
|---|---|---|---|---|---|---|
| 312 g  80 % | 2.5 | 30 min. | 80–85° C | 90 min. | 1250 g | 130 g (90.8 %) |
| 312 g  80 % | 2.5 | 30 min. | 120–130° C | 60 min. | 1250 g | 123.1 g (86 %) |

The results of the different tests indicated above show the undoubted superiority of the process according to the invention over the processes suggested by the prior art.

The temperature range proposed within the scope of the present invention is very accessible and capable of being used on the industrial scale.

Heating to 120°–130° C. can, in fact, be very easily carried out by steam at the pressure of 3 kg/cm², whereas a temperature of 145°–155° C. cannot be produced with such a steam pressure, but on the contrary with steam at 10 kg/cm², which is decidedly more costly.

In conclusion, the process of the invention has been found to be better than the previously mentioned conventional process. For example, the process of the invention comprises only five stages, each of them being carried out by a single operating procedure. Furthermore, the process of the invention only leads to the formation of a minimum of impurities which can be easily eliminated. Finally, the process of the invention is particularly inexpensive: the cost price of the di-n-propyl acetamide prepared by the process of the invention is two to two and a half times less than that according to the conventional process.

The following non-limitative Examples illustrate the process of the invention:

EXAMPLE 1

Preparation of di-n-propyl acetamide (a) Di-n-propyl cyanacetic acid

First of all, a solution of sodium n-propylate was prepared from 7.42 g (0.322 mol) of sodium and 180 ml of anhydrous n-propanol, by heating with gentle reflux until all the sodium had dissolved.

Into a 500 ml spherical flask, equipped with a supply funnel, a mechanical stirrer, a thermometer and a condenser above which was a calcium chloride trap, were introduced 16.95 g (0.141 mol) of ethyl cyanacetate and 40.69 g (0.33 mol) of n-propyl bromide. This mixture was heated to 45° C. and then there was added, slowly and while stirring, the previously prepared solution of sodium n-propylate, the temperature of the reaction medium being maintained at 50°–55° C. by gentle external cooling.

When the operation of introduction was completed, the temperature of the mixture was brought under reflux in 30 minutes and was maintained in this state for 3 hours. The n-propanol was then distilled and the distillation stopped when the temperature of the residual mass had reached 115° C.

The crude ester obtained in this manner was then treated with a solution of 7.5 g of sodium hydroxide in the form of flakes in 67.5 ml of water. The mixture was placed in a 250 ml spherical flask equipped with a condenser, and then the reaction medium was slowly brought to 60°–70° C. This temperature was maintained for 3 1 hours, followed by cooling to about 50° C. and elimination under a pressure of 70 mm/Hg of the ethanol formed and the residue of n-propanol. The solution thus obtained was cooled to 20° C. and acidified, while being stirred, by the addition of 26.25 g of 36% hydrochloric acid. During this operation, the temperature of the reaction medium was kept below 40° C. by cooling. Stirring was maintained for 30 minutes and then the medium was left standing for 30 minutes. The oily later of di-n-propyl cyanacetic acid was decanted and then the aqueous phase was extracted with 35 ml of toluene.

The toluene extract was added to the decanted di-n-propyl cyanacetic acid, whereafter the toluene solution was washed in a decantation funnel with a solution of 1.5 g of sodium chloride in 14 ml of water. The toluene phase was decanted and the toluene distilled under atmospheric pressure.

In this manner, 25 g of crude di-n-propyl cyanacetic acid were obtained.

(b) Di-n-propyl acetonitrile

Into a 100 ml spherical flask equipped with a thermometer and a condenser were introduced 25 g of crude di-n-propyl cyanacetic acid obtained according to the method described above and the mixture was heated on an oil bath.

Decarboxylation commenced at a temperature close to 140° C. The mixture was then brought to reflux temperature, that is to say to the region of 160° C. and then to 190° C. in 2 hours. This temperature was maintained until the release of gas had ended, which lasted 2 hours. The di-n-propyl acetonitrile thus formed was then slowly distilled and the fraction passing over between 165° C. and 175° C. was collected. A second distillation was then carried out.

In this way, 14.7 g of di-n-propyl acetonitrile were collected. B.P. 170° C. Yield: 83% relatively to the ethyl cyanacetate used.

(c) Di-n-propyl acetamide

In a 100 ml spherical flask equipped with a mechanical stirrer, a condenser and a thermometer were mixed 10 g (0.08 mol) of di-n-propyl acetonitrile, obtained by the previously described method, and 25 g of 80% sulphuric acid. The mixture was heated to 80° to 82° C. and kept at this temperature for 2 hours. The reaction medium was cooled to about 15° C. and poured into 100 ml of water at a speed such that the temperature of the medium did not exceed 25° C. This was followed by cooling to about 0° to 2° C. and the mixture was left standing at this temperature for 1 hour. The crystals of di-n-propyl acetamide thus formed were then suction-filtered and washed with 20 ml of water. The crystals were dried and in this way there were obtained 10.98 g of crude di-n-propyl acetamide, representing a yield of 96%.

The crude di-n-propyl acetamide thus obtained was purified by being dissolved under heat in toluene and washed with a aqueous solution of sodium bicarbonate until a pH value close to 7 of the aqueous phase was obtained, and then with water until the sulphate ions had been completely eliminated. The toluene phase was then cooled to 60° C. and active carbon added thereto for decolorising purposes. The toluene solution was heated for one hour under reflux and then dried by azeotropic distillation of the water. The active carbon was then filtered and the filtrate cooled to −10° C. The precipitate which formed was suction-filtered and then dried.

Purification of the di-n-propyl acetamide can be effected in a similar manner in methylene chloride to remove the sulphate ions. This solvent is then eliminated, the residue is taken up under heat by dichloroethane and the solution decolorised with active carbon.

The di-n-propyl acetamide crystallised by cooling and the crystals obtained were suction-filtered.

In this manner, according to whether one or other of these purification methods was used, there were obtained 10.1 to 8.92 g of di-n-propyl acetamide, which represent yields of 91.5% and 90.5%, respectively.

Hydrolysis yield: 87 to 88%, relatively to the di-n-propyl acetonitrile used.

EXAMPLE 2

Preparation of di-n-propyl acetamide

Into a 500 ml spherical flask equipped with a stirrer, a thermometer, a reflux condenser and a dropping funnel were introduced 312 g of 80% sulphuric acid (2.5 g of acid/g of nitrile). While stirring, and over a period of 15 minutes at the approximate temperature of 40° C., there were added 125.2 g of di-n-propyl acetonitrile. The temperature of the reaction medium was raised to 80°–85° C. in 30 minutes and maintained for 90 minutes. The reaction medium was cooled to room temperature and the mixture poured progressively, while being cooled, into a 2000 ml spherical flask containing 1250 g of iced purified water, which was kept stirred so as to obtain a dilution of the acid of about 16%. During this operation, the temperature of the mixture was limited to 25° C. The mixture was then cooled, whereafter the formed crystals were suction-filtered after a temperature from 0° to −5° C. had been maintained for one hour. Rinsing was stirred out on a Buchner funnel by means of two fractions, each of 125 g, of iced purified water, and then the mass of moist product was taken up in a 1000 ml spherical flask containing 620 g of toluene. The mixture was brought, while being stirred, to the reflux of the toluene/water azeotrope (B.P.: 84° C.) until complete dissolution. The lower aqueous phase was decanted, the organic layer was washed under reflux, while being stirred, for 15 to 30 minutes and then decantation was effected with 125 g of purified water containing 6.25 g of sodium bicarbonate, and then with as many fractions of 125 g of purified water as were necessary to remove the sulphate ions in the effluent. The toluene solution was then treated under reflux for 30 minutes with 4.4 g of active carbon, while the water was eliminated by means of the Dean-Stark system. Filtration was carried out, followed by hot rinsing with 62 g of toluene. The filtrate and the rinsing liquid were combined in a second 1000 ml spherical flask, crystallisation was carried out by icing with stirring and this was followed by suction-filtration after a temperature between −5° C. and −10° C. had been maintained for 2 hours.

Rinsing was performed on a Buchner funnel by means of two fractions, each of 62 g, of filtered and iced toluene. Suction-filtration was carried out to a maximum, followed by drying to a constant weight in a ventilated oven at 50° C. In this way, a first fraction of 126 g of di-n-propyl acetamide was obtained, representing a yield of 88.0% with respect to the di-n-propyl acetonitrile used.

The toluenic mother liquors resulting from the suction-filtration and rinsing operations were then brought to dryness near reduced pressure (50° C., 20 mm/Hg.). In this way, 4 g of dry extract formed of di-n-propyl acetamide were obtained in crystal form, which represents an additional yield of 2.8%. Using this method, the di-n-propyl acetamide was obtained with a total yield of 90.8% relatively to the di-n-propyl acetonitrile used.

By recycling the toluenic mother liquors, the di-n-propyl acetamide could be obtained with a yield of 96%.

We claim:

1. In a process for preparing di-n-propyl acetamide of the formula:

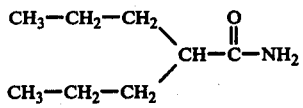

by hydrolysis of di-n-propyl acetonitrile, the improvement whereby di-n-propyl acetonitrile is hydrolysed by means of an 80% sulphuric acid aqueous solution in the proportion of 2.5 grams of said acid per gram of nitrile, at a temperature between 80° C. and 85° C. to produce the desired amide.

2. Process according to claim 1, whereby the hydrolysis reaction lasts from 60 to 90 minutes.

* * * * *